(12) United States Patent
Gunji

(10) Patent No.: US 7,683,915 B2
(45) Date of Patent: Mar. 23, 2010

(54) IMAGE DISPLAYING APPARATUS AND METHOD THEREOF

(75) Inventor: Norihiro Gunji, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 621 days.

(21) Appl. No.: 11/370,148

(22) Filed: Mar. 8, 2006

(65) Prior Publication Data
US 2006/0203131 A1 Sep. 14, 2006

(30) Foreign Application Priority Data
Mar. 8, 2005 (JP) .............................. 2005-063855

(51) Int. Cl.
G09G 5/00 (2006.01)
H04N 1/46 (2006.01)
H04N 1/387 (2006.01)
G06K 9/64 (2006.01)
G06K 9/32 (2006.01)
G06F 3/048 (2006.01)

(52) U.S. Cl. .................. 345/619; 345/649; 345/653; 345/418; 358/537; 358/452; 382/276; 382/295; 382/296; 715/700; 715/764; 715/799

(58) Field of Classification Search ................ 345/649, 345/619, 418–420, 581, 629–630, 650–659; 382/132, 254, 276, 291, 293, 295–297; 600/416; 715/730, 273, 275, 700, 764, 765, 788, 799; 358/537–538, 452–453
See application file for complete search history.

(56) References Cited

U.S. PATENT DOCUMENTS

| 4,730,351 | A | * | 3/1988 | Heumann | 378/98.5 |
| 6,055,326 | A | * | 4/2000 | Chang et al. | 382/132 |
| 6,888,546 | B1 | * | 5/2005 | Kim | 345/419 |
| 2006/0004283 | A1 | * | 1/2006 | Moriyama et al. | 600/416 |
| 2006/0025679 | A1 | * | 2/2006 | Viswanathan et al. | 715/730 |

FOREIGN PATENT DOCUMENTS

JP    2004-173839    6/2004

* cited by examiner

*Primary Examiner*—Wesner Sajous
(74) *Attorney, Agent, or Firm*—Oblon, Spivak, McClelland, Maier & Neustadt, L.L.P.

(57) ABSTRACT

An image displaying apparatus and method thereof for displaying on a monitor an original image generated based on image data of an object acquired through an image radiography apparatus together with posture data for the original image that is acquired at a radiography time. The image displaying apparatus and method includes a function unit and/or a function configured to rotate the original image centering on an axis in order to dissolve a displacement between a first (reference) posture data that is acquired based on the image radiography apparatus and/or a bed unit for supporting the object, and actual posture of the original image. The function unit further displays a second (actual) posture data that is acquired by the rotation of the original image by replacing the first (reference) posture data.

19 Claims, 6 Drawing Sheets

IMAGE DISPLAYING APPARATUS AND METHOD THEREOF

CROSS-REFERENCE TO RELATED APPLICATIONS

This application claims priority from, and the benefit of, Japanese Patent Application No. 2005-63855, filed on Mar. 8, 2005, the contents of which are expressly incorporated herein by reference in their entirety.

BACKGROUND OF THE INVENTION

A. Field of the Invention

The present invention relates to an image displaying apparatus and image displaying method thereof for applying to an image radiography apparatus, and more particularly to an apparatus and method for displaying two dimensional radiographic images or three dimensional radiographic images of an object (patient) which are acquired through a medical image radiography apparatus and for displaying together with posture data or posture marks for indicating directions of the two dimensional-radiographic images or three dimensional-radiographic images on the same screen of a monitor.

B. Background of the Invention

X-ray diagnosis apparatuses, such as an X-ray CT apparatus and a magnetic resonance imaging apparatus, are used to display radiographic images of body insides of a patient in order to observe states of diseases or injuries. This is very important for deciding a policy of medical treatment or an operation plan. In accordance with developments of recent computer technologies, it becomes possible to display images that are reconstructed in real time based on image data collected through a medical image radiography apparatus on a monitor. It is also possible to display not only two dimensional-images but also three dimensional-images, such as an multi-planer reconstruction (MPR) image on the monitor. Since it becomes possible to easily specify a morbid position, three dimensional-images are useful for deciding an operation plan.

Usually, as illustrated in FIG. 6, an object (patient) 1 is lying on a top plate 3 of a bed apparatus 2, and the image data collection through a medical image radiography apparatus is performed by sliding the top plate 3 to a radiography position in an image radiography apparatus 4 with keeping the object 1 in such a horizontal lying posture. To easily and correctly observe or diagnose a reconstructed image of the acquired image data displayed on a monitor, it needs to display lying posture data or posture indicating marks for the image data that indicate the posture or directions of the object 1 at a radiography time also displayed on the same screen with attached to the reconstructed image.

The characters or marks for indicating the posture data are primarily decided based on the coordinates or the direction cosines of the position of the top plate or the bed apparatus for supporting the object at a time of image radiography. Generally, the coordinates are decided by the irradiation axes (as shown by the X axis and Y axis in FIG. 6) that pass through an irradiation center of the image radiography apparatus and a sliding center axis of the sliding top plate 3 of the bed apparatus (as shown by the Z axis in FIG. 6). Hereinafter, the posture data that is primarily decided by these reference coordinates is referred as a first posture data.

The posture data displayed on a monitor together with a reconstructed image is represented by a state of characters or marks. FIG. 7 explains an example of the posture data that are acquired by placing the top plate 3 supporting an object 1 at a radiation center position of the image radiography apparatus. As an exemplary posture data, a character "A" indicates a front abdomen side of the object 1, a character "P" is a posture data indicating a direction of a back side of the object 1. Similarly, the characters "R" and "L" indicated right and left directions of the image of the object lying on the tap plate, respectively. Further, the characters "H" and "F" (not shown), will be added to indicate posture date for a three dimensional image in order to respectively indicate a head side and a foot side of the object, respectively.

FIG. 8 illustrates an example of a radiographic three-dimensional image 1a of a head portion of an object 1 and posture data displayed around the head portion image 1a on a monitor. The head portion image 1a is reconstructed by an image processing apparatus based on image data that is collected through an image radiography apparatus 4, as e shown in FIG. 6. At a radiography time, posture data of the head portion also acquired through an image radiography apparatus 4 based on coordination of a top plate for supporting an object. The posture data are provided around the image 1a so as to indicate the direction of the image 1a. As the posture data or posture mark, four characters "A", "R", "P" and "L" are displayed on a monitor of the image display apparatus. Since various other reference data may also be displayed on a screen of the monitor 5 in addition to the posture data, it is desirable to render displaying items as small as possible in order to easily read a screen. Since either one of a front face or a back face, and either one of right or left are indicated, the other position is automatically understood, it is sufficient to display only two characters or marks for indicating as the posture data on a monitor. Usually, characters "R" and "P" are displayed on the monitor and opposite direction indicating characters "A" and "L" are often omitted.

The displayed posture data provided around a reconstructed image on a monitor is not aimed to indicate a precise angle of an object, but to simply show the directions for the posture of the object. In FIG. 8, a coordinate axis is shown by a dotted line for only using a better understanding of the invention. Accordingly, such a coordinate axis need not be displayed on an actual monitor.

As explained above, the posture data displayed on a monitor 5 together with a reconstructed image is primarily decided based on the coordinates or the directions of a bed apparatus 2 and/or a top plate 3 during radiography of the image. Accordingly, it is desirable to place an object on the plate so as to be placed in a horizontal direction facing toward a perpendicular direction of the plate. However, due to the status of the patient's injury or sickness, the object might not be able to take such a horizontal posture with facing right upward on the top plate. In such a case, it is inevitable to take radiography even though the actual posture of the object 1 is laying at a displaced position different from the coordinates for the bases of the first posture data. Consequently, a displacement may appear between the reconstructed original image and the first posture data displayed on the monitor 5.

FIG. 9 illustrates an example of such a case. Thus, it is impossible for a patient to turn his head towards a perpendicularly top direction, and the head of the patient is placed with tilting around 40 degrees toward a right side of his body that is different from the coordinate axis A based on the irradiation axis of the image radiography apparatus. The image data is acquired at this situation and the original reconstructed image displayed on a monitor screen. When the radiography is executed with displacing a patient's posture from a prescribed coordinate positions, as shown in FIG. 9, an original reconstructed tomography image 1a is displayed with tilting toward the posture data "L". On the contrary, the display of the first posture data is preliminarily decided with no relation to the actual posture of the object. Accordingly, the reconstructed original image and the first posture data are displayed on the monitor with appearing a displaced relationship between them. Such a displacement between the reconstructed original image and the first posture data causes difficulties of the observation or errors of diagnosis. To avoid such difficulties, one conventional technique has been ignored even though some degree of the displacement is present between the reconstructed original image and the first posture data. Another conventional technique changes a posture data displaying mode from a "normal mode," in which the posture data is set to be usually displayed, to an "other mode" in which the posture data is disappeared from the monitor screen and the original reconstructed image only has been displayed. However, when the original reconstructed image is observed with attaching no posture data at a radiography time, in particular when a three dimensional image, it may happen that a right and a left direction are misunderstood. To avoid such a misunderstanding, an observer i.e., a doctor, is required to correct the image position in his brain in order to diagnose or to plan an operation. Thus, this places a big burden on the observer, and it also is a cause of an error for diagnosis.

SUMMARY OF THE INVENTION

The present invention solves the above-mentioned undesirable problems and defects and reduces the burden on the observer to correct posture data. Further, the present invention prevents such an error of diagnosis from occurring due to non-display of the posture data. The present invention provides image displaying apparatus and method thereof that can correct a displacement appeared in a relationship between a reconstructed original image and the first posture data when it is impossible for an object to lay on the prescribed coordinate for a basis of a posture data. The image displaying apparatus and method thereof consistent with the present invention can display the corrected posture of the object as a second posture data on a monitor by replacing the first posture data so as to easily understand that the displayed posture data has been corrected.

To solve the above problems and defects, an embodiment of the present invention includes an image displaying apparatus including a monitor and a display function unit for displaying an original image that is reconstructed based on image data of an object acquired through an image radiography apparatus, and for displaying first posture data of the original image determined based on coordinates or direction cosines of at least one of the radiography apparatus and a supporting means for the object, wherein the display function unit comprises: an image rotating operation unit configured to rotate the original image by centering the image on a reference axis among the coordinates or direction cosines on the monitor along a predetermined direction within a predetermined angle, so as to reduce a displacement between the first posture data and an actual posture of the object at a time of radiography; a decision unit configured to determine the rotated position of the original image as second posture data for the rotated original image in order to correct the displacement; and a posture data correcting unit configured to display the decided second posture data on the monitor together with the rotated original image by replacing the first posture data on the monitor.

An embodiment of the present invention includes an image displaying method for displaying on a monitor an original image reconstructed based on image data of an object acquired through an image radiography apparatus, and for displaying first posture data of the original image determined based on coordinates or direction cosines of at least one of the radiography apparatus and a supporting means for the object, the method comprising: rotating the original image by centering on a reference axis among the coordinates or direction cosines on the monitor along a predetermined direction within a predetermined angle so as to reduce a displacement between the first posture data and an actual posture of the object at a time of radiography; determining the rotated position of the original image as second posture data for the rotated original image in order to correct the displacement; and displaying the decided second posture data on the monitor together with the rotated original image by replacing the first posture data on the monitor.

Another embodiment of an image displaying apparatus consistent with the present invention includes an image radiography apparatus configured to acquire image data of an object and first posture data relating to the image data; a display unit configured to display an image reconstructed based on the acquired image data and to display the first posture data together with the displayed image; a rotation operation unit configured to rotate the displayed image by centering a reference axis along a direction within a prescribed angular range; a correction operation unit configured to correct the first posture data; a decision unit configured to determine second posture data of the rotated original image so as to reduce a displacement between an actual posture of the object and the first posture data; and a posture correction unit configured to display the determined second posture data and the rotated original image together on the display unit by replacing the first posture data.

The image displaying apparatus consistent to the present invention includes a rotation operation unit configured to rotate a two-dimensional original image around a reference axis of a perpendicular coordinate to a horizontal face of the top plate for supporting the object within a prescribed range, the rotation operation unit configured to rotate a three-dimensional original image around the reference axis of the perpendicular coordinate to the horizontal face of the top plate and also around each of two reference axes that are respectively determined by two directional coordinates of the radiography apparatus.

In the image display apparatus consistent with the present invention the image rotating operation unit rotates a two-dimensional original image centering on a reference center axis determined by one coordinate along a sliding direction of the bed unit for supporting the object, and wherein the image rotating operation unit rotates a three-dimensional original image centering on each of three reference center axes, one of which is determined by one coordinate along the direction of the bed unit and the remaining two axes are determined along the two coordinates that are determined by the image radiography apparatus.

According to the image displaying apparatus and method thereof consistent with the present invention, it become possible to immediately observe a reconstructed image together with correct posture data without manually considering the correction of the posture data. Thus, it becomes possible to reduce burden of the observer for performing quick and correct diagnosis.

According to the image displaying apparatus and method thereof consistent with the present invention, it become possible to easily correct posture data when a displacement appears in a relationship between a first posture data that is primarily decided by apparatus and an actual posture of the reconstructed original image.

According to the image displaying apparatus and method thereof consistent with the present invention, it become possible to clearly identify a difference between a first posture data that is primarily decided by an apparatus and a second posture data that is corrected so as to dissolve a displacement and indicate the actual posture of the reconstructed original image. Thus, it becomes possible for an observer to execute high efficiency in diagnosis and to perform a accurate operation planning.

According to the image displaying apparatus and method thereof consistent with the present invention, a rotation of the reconstructed original centering on a reference axis is limited within a certain range so as to avoid excessive rotation of the image. Accordingly it become possible to avoid correction errors due to an excessive rotation of the image.

According to the image displaying apparatus and method thereof consistent with the present invention, it become possible to transfer the reconstructed original image and the corrected posture data to another work station so as to display the same corrected posture data. Thus, it becomes possible to observe the same data for deciding by many of observers.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings.

DESCRIPTION OF THE EMBODIMENTS

Figure 1:
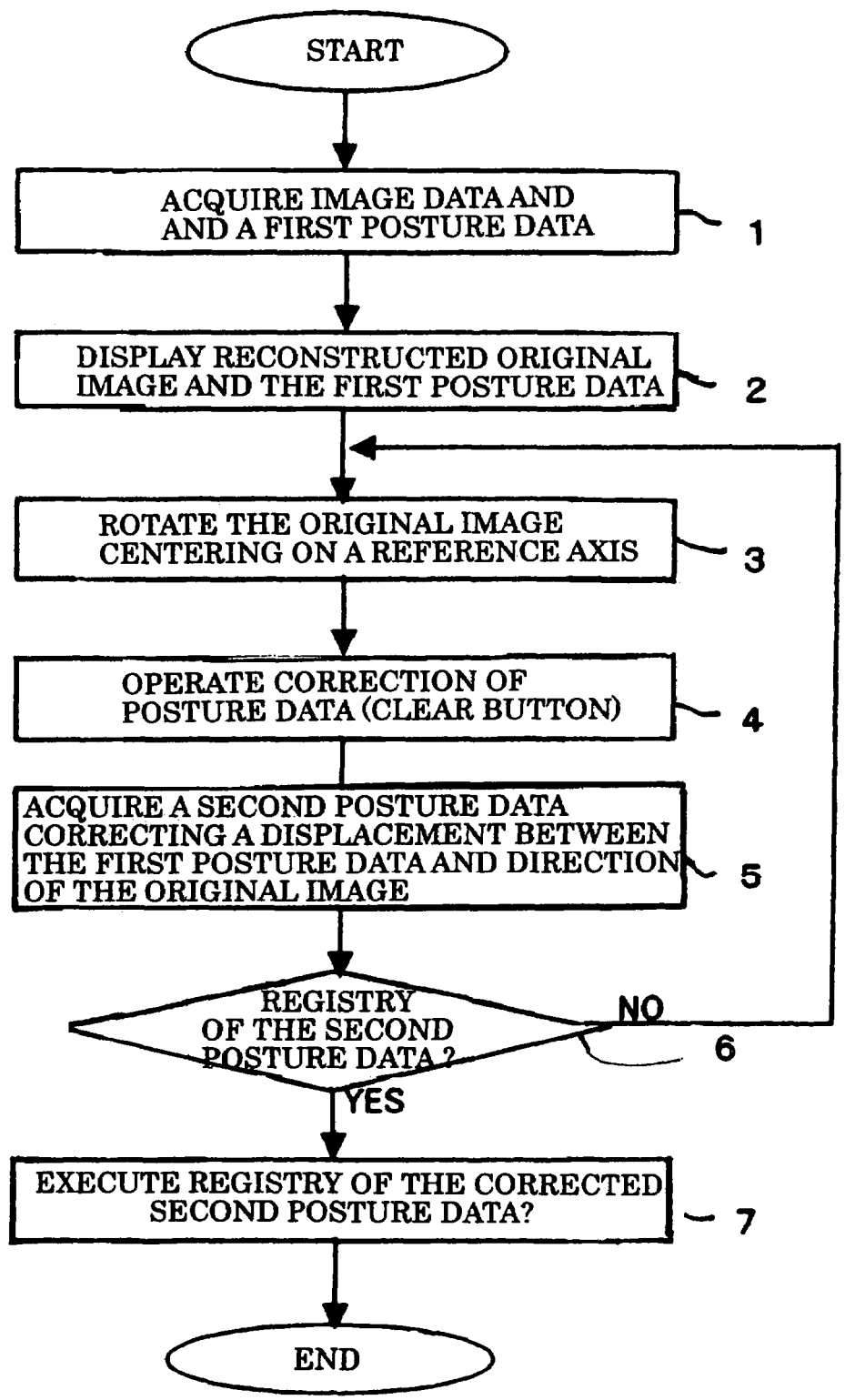
FIG. 1 is a flowchart for explaining an embodiment of the image display apparatus and method consistent with the present invention.

With reference to FIG. 1-9, an embodiment of an image displaying method consistent with the present invention is explained. FIG. 1 is a flowchart explaining the embodiment according to the present invention. Each of FIGS. 2-5 is a two-dimensional cross-section view explaining a screen state of a monitor in a display apparatus with regard to the respective steps of FIG. 1.

Figure 6:
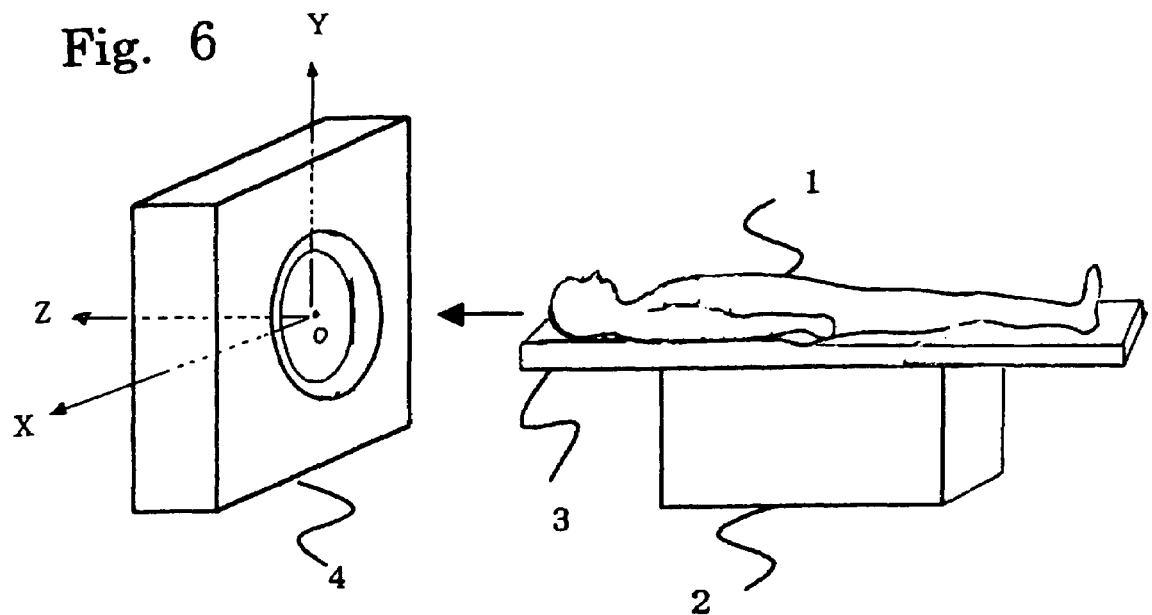
FIG. 6 illustrates acquisition of original image data of an object and first posture data for the original image data through a medical image radiography apparatus.
Figure 7:
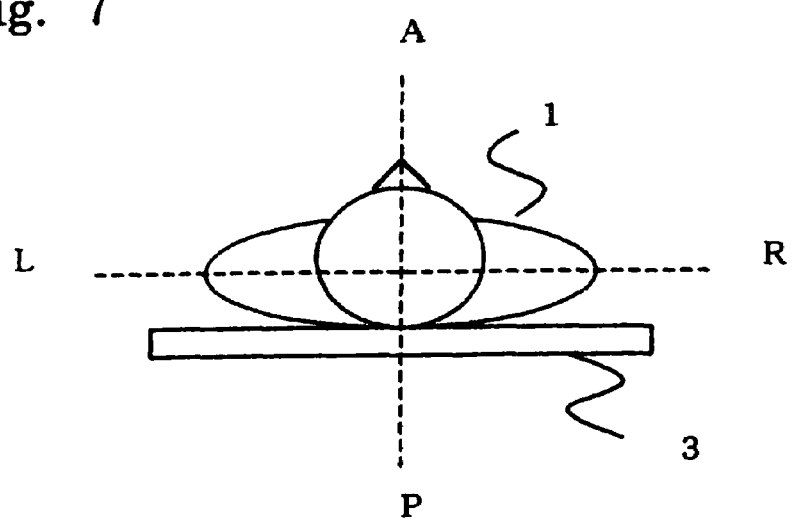
FIG. 7 is an example for illustrating a first posture data of the object lying on a top plate.
Figure 8:
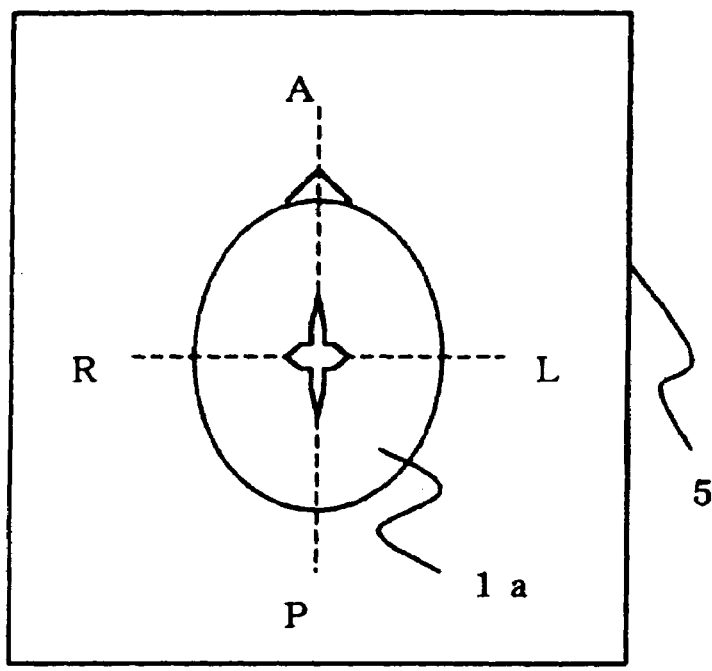
FIG. 8 is a model showing a cross-sectional image of a head portion of the object and first posture data of the image.
Figure 9:
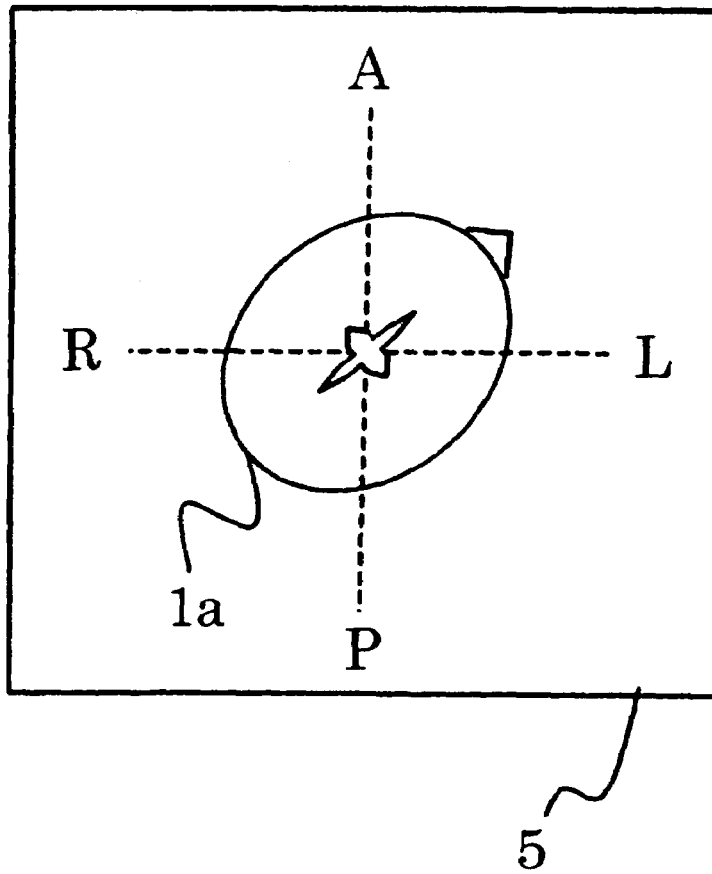
FIG. 9 illustrates a cross-sectional image of a head portion of the object and first posture data of the image that are acquired when the head of the object is tilted at the time of radiography.

To simplify the explanation, as shown in FIG. 6, the present embodiment supposes that two-dimensional cross-section image data of a head portion 1a of an object 1 and posture data of the image are acquired by sliding the object 1 laying on a top plate 3 of a bed apparatus 2 (as shown in FIG. 6) into a radiography position of an image radiography apparatus 4, such as an X ray computer tomography (CT) apparatus or a magnetic resonance imaging (MRI) apparatus. Due to a state of injury or sickness, it is impossible for the object 1 to horizontally keep his head portion 1a to the top plate 3 so as to face vertically upward. Suppose that the head portion 1a is tilted to a left side around 40 degrees from a perpendicular axis of the top plate 3.

Figure 2:
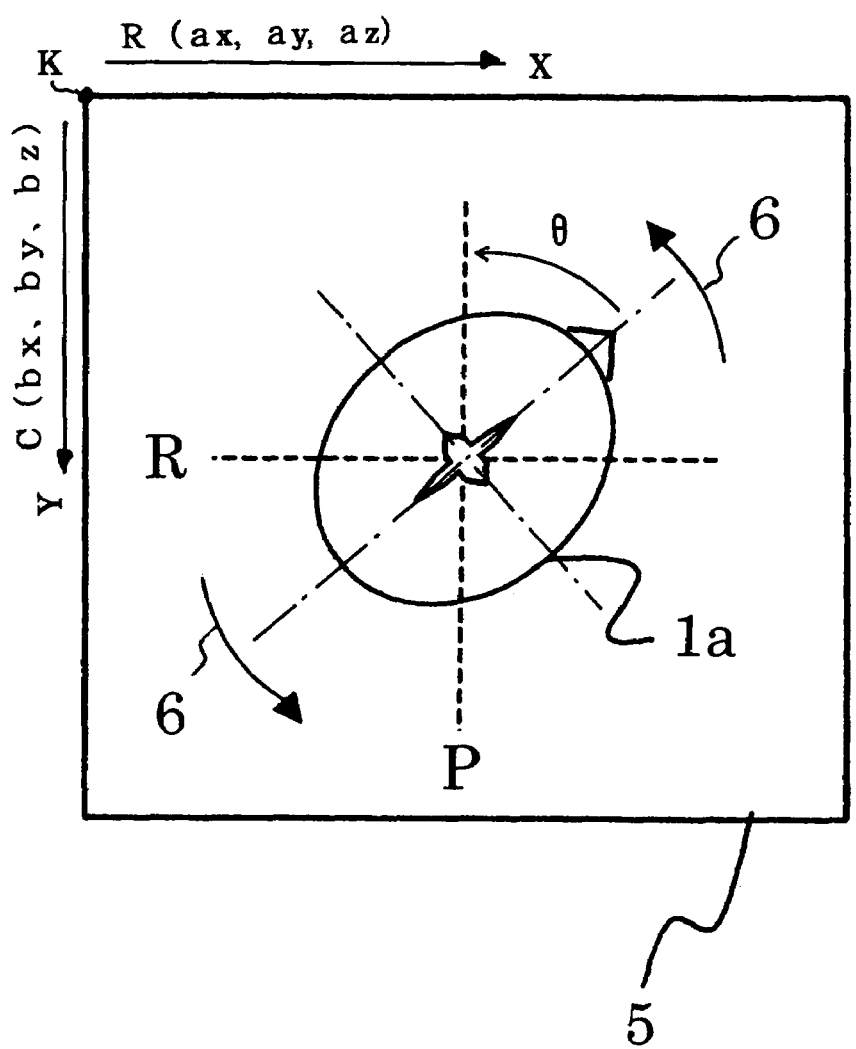
FIG. 2 illustrates a rotation of an example display of an original image and first posture data acquired through an image radiography apparatus.

In an embodiment of the image displaying apparatus and method thereof consistent with the present invention, at a radiography time, two-dimensional cross-section original image data and first posture data for the original image data are acquired together (step 1). The first posture data is primarily acquired based on coordinates or direction cosine of the image radiography apparatus 4 including the coordinate of the top plate 3. As shown in FIG. 2, a reconstructed tomography image 1a generated based on the acquired original image data and the first posture data are displayed on a monitor screen. In this example, the first posture data displayed on a screen by characters "R" and "P" at a prescribed positions (step 2). The character "R" of the first posture data indicates a right side of the object image decided by a reference coordinate of the radiography and the character "P" indicates a back side of the tomography image 1a of the object.

As shown in FIG. 2, in the embodiment of the present invention, a two-dimensional cross-section original image 1a is actually displayed on a monitor with inclination toward a left direction from a reference Y axis for the radiography apparatus. Accordingly, the actual posture of the image appears displaced from the first posture data "R" and "P" that are primarily decided by the reference coordinates of the radiography apparatus. Under this status of the display, it is difficult to perform diagnosis. Accordingly, an observer, such as a doctor, intends to rotate the radiography original image into a correct position suitable for accurate observation. In this embodiment, consistent with the present embodiment, the original image 1a is rotated in a counter-clockwise direction (as shown by an arrow) so that a front of the image is aligned with a reference X axis of the radiography apparatus. The rotation of the image is performed by operating a rotation knob in an operation unit while viewing the original image 1a displayed on the monitor 5 so that the original image 1a rotates centering on a reference Z axis until a front of the original image 1a faces to a top of the screen (step 3).

For a person skilled in the art, it is a well known technique to rotate an image on a monitor. Accordingly, the detail explanation of the rotation of the image is omitted. However, in consideration of safety, this embodiment of the present invention has a limited range for the posture correction of the image in order to prevent an excessively correcting rotation of the image. For instance, a permissible rotation angle is limited in a range of plus 45 degrees to minus 45 degrees. By limiting the range of correcting rotation, it becomes possible to prevent an error correction of the posture data due to an excessive rotation of the image. Consequently, it becomes possible to prevent misdiagnosis or error planning of an operation from occurring.

Figure 3:
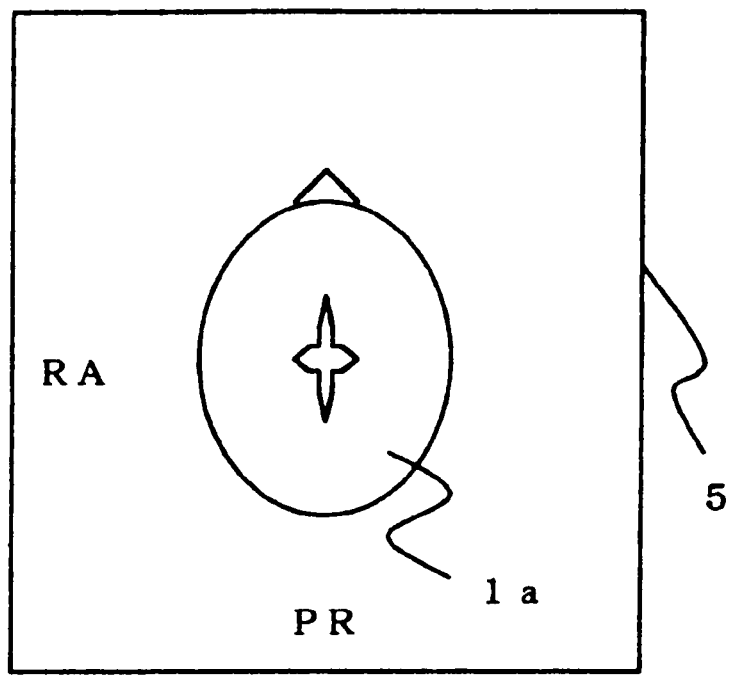
FIG. 3 illustrates a rotated original image in a correcting direction.

FIG. 3 shows a monitor screen 5 in which a head portion 1a of the object has been rotated so as to face a front (a top direction of the screen). The actual back side posture of the original image 1a has originally positioned at a middle position between the first posture data "P" and "R". Accordingly, the actual posture data of the rotated original image 1a should be displayed as characters "PR" for indicating a middle position of "P" and "R", Similarly, an actual left side posture data for the rotated original image 1a should be displayed as characters "RA" for indicating a middle position of "R" and "A". Although not shown in FIG. 3, a rotated front posture data becomes "AL" and a rotated right side posture data of the original image 1a becomes "LP".

If an original image is a three-dimensional image, the rotation of the original image is performed by respectively centering on each of a reference X axis, a reference Y axis, and a reference Z axis that are primarily decided by the coordinates of the radiography apparatus and the bed apparatus. It is also possible to calculate the posture data of the three-dimensional image by using a direction cosine. The direction cosine is determined, for example, as shown in FIG. 2, that a position D of one top corner of the screen left side top is represented by the directions R(ax, ay, az), and C (bx, by, bz). Such a three-dimensional display can easily illustrate a status or a position of injury or disease by a visual recognition of the rotation amount.

Figure 4:
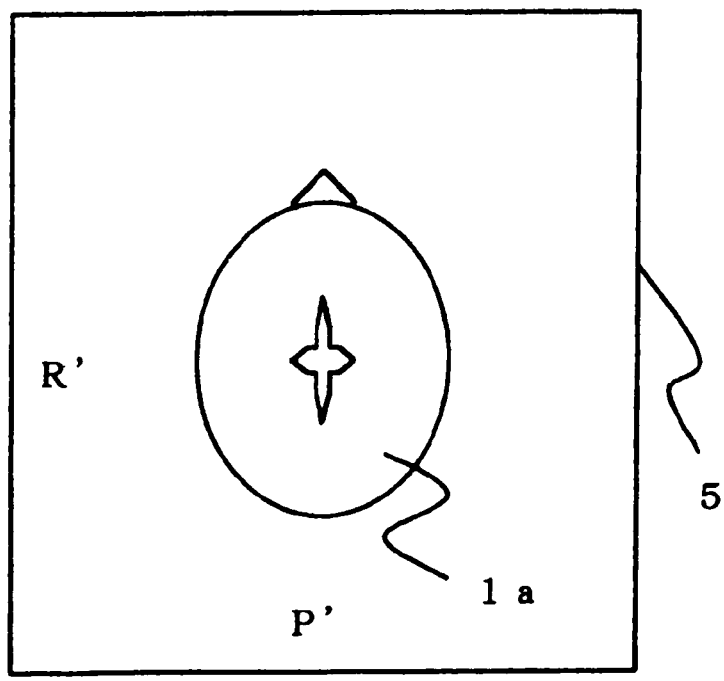
FIG. 4 is an example of second posture data for the rotated original image of FIG. 3.

After performing the correcting rotation of the original image at Step 3, a posture data correction is executed by clicking a posture correction button (zero clear button) or knob in an interactive screen on the monitor (step 4). By rotating the original image 1a to a desired direction in a limited range, second posture data that resolves a displacement of a relationship between the first posture data and the original image 1a (step 5). Thus, as shown in FIG. 4, a corrected new posture data (actual posture data) [P'] and [R'] are displayed at a bottom side and a left side of the rotated original image 1a, respectively, as second posture data.

In this embodiment, the corrected second posture data (actual posture data) [R'] and [P'] are respectively represented by affixing a mark ['] to each of the first posture data "R" and "P" in order to identify the corrected second posture data for an observer. Of course, it is also possible to change characters, marks, or forms for the corrected second posture data. Further, it is possible to change a color of the second posture data from the one for the first posture data. In a three-dimensional image, it is possible to display the posture data in a cubic body identifying a front side and showing an amount of the rotation at some of the sides of the cubic. By displaying the corrected second posture data in a different form from the first posture data, it can clearly be recognized that the posture of the original image has been rotated. Consequently, it can prevent a misunderstanding or an error of diagnosis due to misunderstanding of the posture data from occurring. Thus, an observer, e.g., a doctor, can execute an accurate and efficient diagnosis and planning of an operation.

Figure 5:
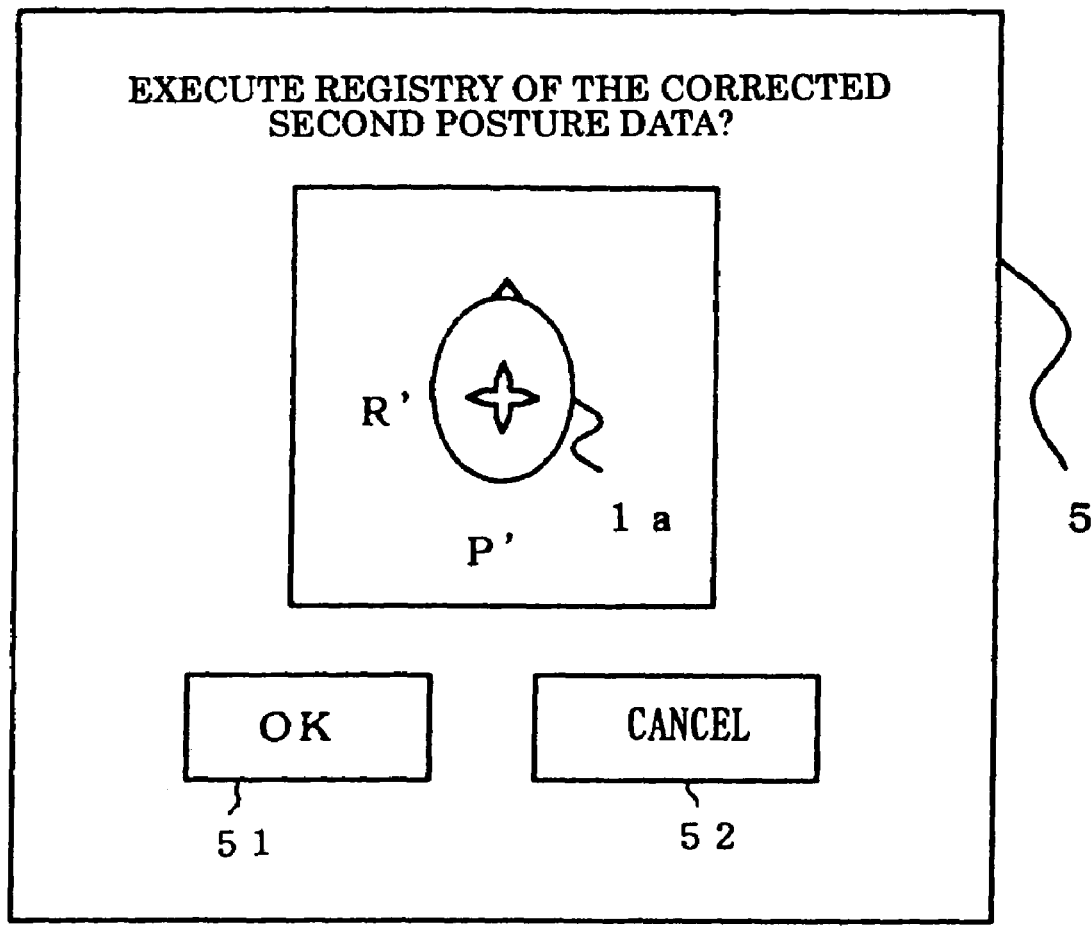
FIG. 5 is an example of an interactive monitor screen for deciding a registration of the second posture data of FIG. 4.

To display the corrected second posture data obtained at Step 5 by replacing the first posture data on the monitor, a registration operation of the second posture data must be performed. To do so, the operator clicks a registration (zero clear) button provided on the display unit (step 5). When the registration (zero clear) button is clicked, an interactive screen 5, such as shown in FIG. 5, is displayed on the monitor. The operator confirms the second posture data on the screen and confirms whether or not the second posture data should be registered (step 6). When the operator confirms the registration of the second posture data (step 6, YES), the operator clicks an OK button 51 in the interactive screen 5 and the registration of the second posture data is performed (step 7). By registering the second posture data, the posture data changing operation has been finished. If the operator does not confirm the registration of the second posture data (step 6, NO), the operator clicks a cancel button 52 in the interactive screen 5, and the registration operation is suspended and the process goes back to the step 3 in order to again rotate the original image and obtain a new corrected posture data. Thus, in the present embodiment, the registration of the posture data is carefully executed in order to avoid an error of registration of the posture data.

As explained above, the apparatus and method consistent to the present invention are applicable to both original two-dimensional image and three-dimensional images. In a three-dimensional image, if the original image is tilted in three dimensions, the original image is rotated in desired directions by centering on each of reference axes of the three dimensions and by calculating each of direction cosine, the corrected second posture data are obtained. It is also possible to store the corrected (actual) posture data in a storage apparatus as affixed data for a DICOM image, which is a international communication standard for medical digital images. By storing DICOM image data, it becomes possible to transfer the rotated original image and the corrected posture data to another image work station. The transferred images and posture data can be displayed on the transferred work station.

Further, it is possible to display both of the first posture data and the second posture data for the rotated two dimensional image or the three dimensional image together in order to easily compare the difference between the two posture data. If the observer is doubtful, they can easily confirm the posture data.

The images applicable to the apparatus and method consistent to the present invention are not limited to images that are acquired through a medical image radiography apparatus in real time. Of course, it is possible to process images that are stored in a storage apparatus and read out from the storage apparatus.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

What is claimed is:

1. An image displaying apparatus including a monitor and a display function unit for displaying an original image that is reconstructed based on image data of an object acquired through an image radiography apparatus, and for displaying first posture data of the original image determined based on coordinates or direction cosines of at least one of the radiography apparatus and a supporting means for the object,
    wherein the display function unit comprises:
    an image rotating operation unit configured to two or three dimensionally rotate the original image by centering the image on a reference axis among the coordinates or direction cosines on the monitor along a predetermined direction within a predetermined angle, so as to reduce a displacement between the first posture data displayed on the monitor and an actual posture of the object at a time of radiography;
    a decision unit configured to determine the two or three dimensionally rotated position of the original image as second posture data for the rotated original image in order to correct the displacement based on a relative position between the first posture data and a direction of the rotated original image; and
    a posture data correcting unit configured to display the decided second posture data on the monitor together with the two or three dimensionally rotated original image by replacing the first posture data on the monitor.

2. The image display apparatus according to claim 1,
    wherein the image rotating operation unit rotates a two-dimensional original image centering on a reference center axis determined by one coordinate along a sliding direction of the bed unit for supporting the object, and wherein the image rotating operation unit rotates a three-dimensional original image centering on each of three reference center axes, one of which is determined by one coordinate along the direction of the bed unit and the remaining two axes are determined along the two coordinates that are determined by the image radiography apparatus.

3. The image display apparatus according to claim 2, wherein the original image is a two-dimensional image, and the decision unit determines that the second posture data indicates a reference position when the original image is rotated so as to coincide along the reference axis.

4. The image display apparatus according to claim 3, wherein the posture data correction unit displays the three-dimensional original image using the second posture data based on the determined reference positions.

5. The image display apparatus according to claim 1, wherein the posture correction unit displays the second posture data by changing a form or a color of the first posture data.

6. The image display apparatus according to claim 1, further comprising:
a storage unit configured to store at least one of the first and the second posture data as label data of the original image.

7. The image display apparatus according to claim 1, wherein at least one of the first and the second posture data is displayed on the monitor by using a minimum number of labels so as to specify the directions of the posture of the object at a radiography time.

8. The image display apparatus according to claim 6, wherein a two-dimensional image of the original image is represented by characters or marks, and a three-dimensional image of the original image is represented by characters, marks, or a cubic form.

9. The image display apparatus according to claim 6, wherein the display function unit is configured to display the second posture data by replacing the first posture data based on the label data stored in the storage unit, and to display both the first and second posture data together.

10. An image displaying method for displaying on a monitor an original image reconstructed based on image data of an object acquired through an image radiography apparatus, and for displaying first posture data of the original image determined based on coordinates or direction cosines of at least one of the radiography apparatus and a supporting means for the object, the method comprising:
two or three dimensionally rotating the original image by centering on a reference axis among the coordinates or direction cosines on the monitor along a predetermined direction within a predetermined angle so as to reduce a displacement between the first posture data displayed on the monitor and an actual posture of the object at a time of radiography;
determining the two or three dimensionally rotated position of the original image as second posture data for the rotated original image in order to correct the displacement based on a relative position between the first posture data and a direction of the rotated original image; and
displaying the decided second posture data on the monitor together with the two or three dimensionally rotated original image by replacing the first posture data on the monitor.

11. The image displaying method according to claim 10, wherein the rotating step comprises:
rotating a two-dimensional image of the original image around a reference axis along one coordinate of a sliding direction of a bed unit in a prescribed direction; and
rotating a three-dimensional image of the original image around a reference axis along one coordinate of a sliding direction of the bed unit in a prescribed direction, and rotated around each reference axis of two coordinates respectively determined by the radiography apparatus.

12. The image displaying method according to claim 10, wherein the rotating step comprises:
rotating a three-dimensional original of the image so as to face the reference axis, and the determining step comprises determining posture data at the rotated position as a reference position.

13. The image displaying method according to claim 12, wherein the displaying step comprises:
displaying a three-dimensional image of the original image on the monitor by using the second posture data based on the determining reference position.

14. The image displaying method according to claim 10, wherein the displaying step comprises:
displaying the second posture data in a form or color different from the character or mark of the first posture data.

15. The image displaying method according to claim 10, further comprising:
storing at least one of the first posture data and/the second posture data as label data of the original image.

16. The image displaying method according to claim 10, wherein at least one of the first posture data and the second posture data is displayed using a minimum number of directions for specifying a posture of the object at a radiography time.

17. The image displaying method according to claim 14, wherein the displaying step comprises:
displaying the second posture data by replacing the first posture data, or displaying both of the first posture data and the second posture data.

18. An image displaying apparatus, comprising:
an image radiography apparatus configured to acquire image data of an object and first posture data relating to the image data;
a display unit configured to display an image reconstructed based on the acquired image data and to display the first posture data together with the displayed image;
a rotation operation unit configured to rotate the displayed image by centering a reference axis along a direction within a prescribed angular range;
a correction operation unit configured to correct the first posture data;
a decision unit configured to determine second posture data of the rotated original image so as to reduce a displacement between an actual posture of the object and the first posture data based on a relative position between the first posture data and a direction of the rotated original image; and
a posture correction unit configured to display the determined second posture data and the rotated original image together on the display unit by replacing the first posture data.

19. The image displaying apparatus according to claim 18, wherein the correction unit includes a zero clear button; and
the decision unit includes an approval button on an interactive screen of the display unit.

* * * * *